(12) United States Patent
Veres

(10) Patent No.: US 6,439,845 B1
(45) Date of Patent: Aug. 27, 2002

(54) BLOOD PUMP

(75) Inventor: Joseph P. Veres, Westlake, OH (US)

(73) Assignee: Kidney Replacement Services, P.C., Detroit, MI (US)

( * ) Notice: Subject to any disclaimer, the term of this patent is extended or adjusted under 35 U.S.C. 154(b) by 0 days.

(21) Appl. No.: 09/533,335

(22) Filed: Mar. 23, 2000

(51) Int. Cl.$^7$ .................................................. F03B 1/04
(52) U.S. Cl. .................. 415/206; 415/900; 416/223 B; 416/185; 417/420
(58) Field of Search .................. 415/206, 900, 415/204, 200, 229; 416/223 B, 185, 186, DIG. 2, 241; 417/420

(56) References Cited

U.S. PATENT DOCUMENTS

| | | | | |
|---|---|---|---|---|
| 5,316,440 A | * | 5/1994 | Kijima et al. | 415/206 |
| 5,360,317 A | * | 11/1994 | Clausen et al. | 415/206 |
| 5,683,231 A | * | 11/1997 | Nakazawa et al. | 417/420 |
| 5,803,720 A | * | 9/1998 | Ohara et al. | 417/420 |
| 5,863,179 A | * | 1/1999 | Westphal et al. | 415/206 |
| 6,135,710 A | * | 10/2000 | Araki et al. | 415/206 |
| 6,158,984 A | * | 12/2000 | Cao et al. | 417/423.1 |
| 6,183,220 B1 | * | 2/2001 | Ohara et al. | 417/420 |

\* cited by examiner

*Primary Examiner*—F. Daniel Lopez
*Assistant Examiner*—James M McAleenan
(74) *Attorney, Agent, or Firm*—Brooks & Kushman P.C.

(57) ABSTRACT

A blood pump includes a centrifugal impeller for pumping blood and a volute member enclosing the centrifugal impeller within a volute chamber. A magnetic drive causes magnets embedded on the impeller to rotate the impeller. The centrifugal impeller and volute chamber are configured to provide a specific speed ratio (Ns) of between approximately 500 and 600 wherein Ns equals NQ0.5/H0.75, where: N=impeller rotative speed in revolutions per minute (RPM); Q=gallons per minute (GPM) of flow; and H=head rise in feet of blood. The impeller includes blades having a radial length to an axial width ratio that provides the specific speed. The configuration of the volute and impeller combination provides desired blood flow and pressure rise at low specific speed.

17 Claims, 3 Drawing Sheets

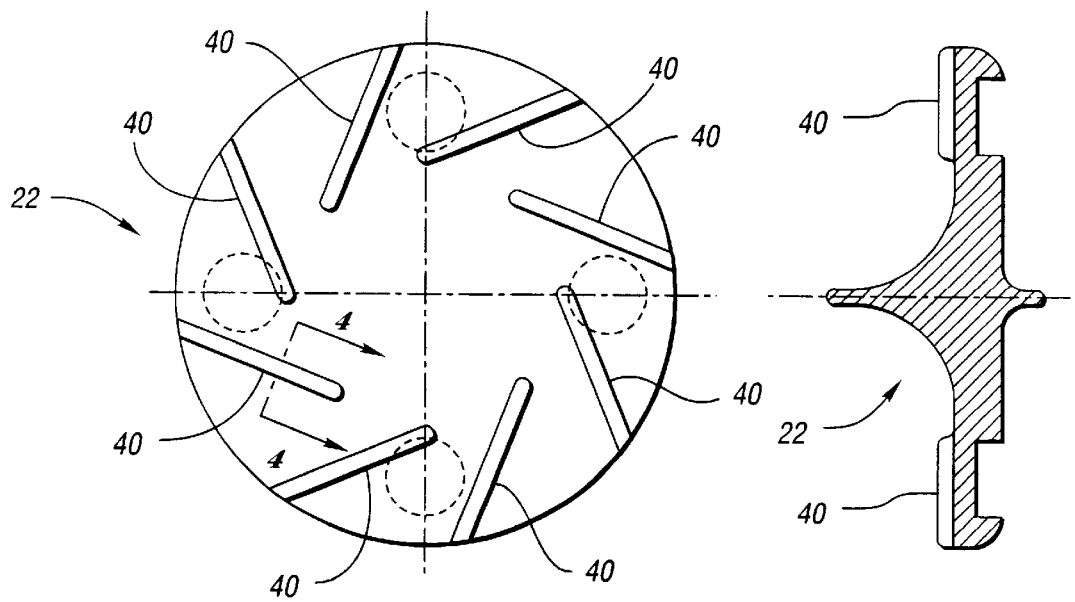
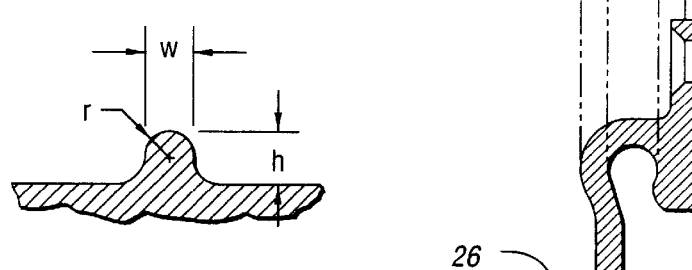
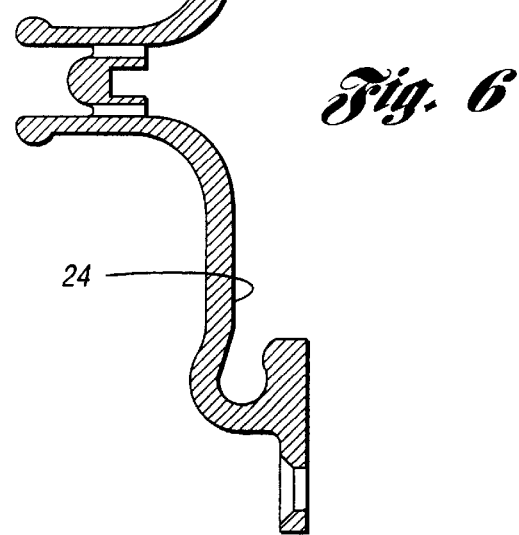
Fig. 3
Fig. 5
Fig. 4
Fig. 6

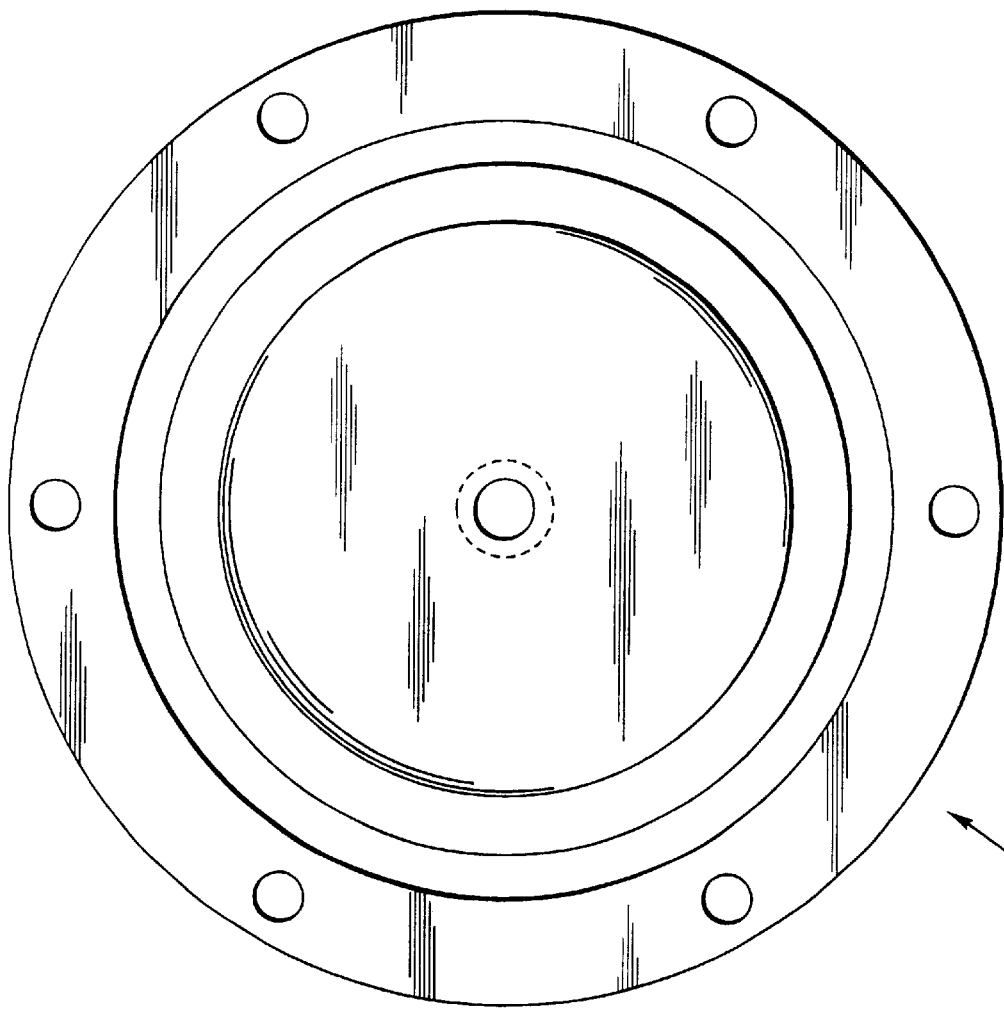

BLOOD PUMP

TECHNICAL FIELD

The present invention relates to a centrifugal blood pump, used for renal replacement therapy or as a left ventricular assist pump, which employs a magnetic coupling for rotating an impeller and is capable of providing desired flow and pressure rise at a very low "specific speed".

BACKGROUND ART

There are approximately 38,000 kidney patients per year who are in need of donor kidneys, but the supply of donated kidneys is merely approximately 8,000 per year. Accordingly, many of these patients use hemo-dialysis machines for filtering toxins from blood. These machines typically require the dialysis patient to be attached to a machine for approximately three hours three times per week. Obviously, this is very burdensome for the patient, and it is therefore desirable to provide an improved dialysis device which is portable and/or implantable, which eliminates the need to be connected to current large dialysis machines.

Current dialysis machines use a peristaltic pump to provide the needed low flow rate. The peristaltic pump is a positive displacement pump including a roller which pushes the blood through a rubber tube as it rolls along and compresses the tube. The peristaltic pump is very large in size and is therefore less feasible to be portable or implantable due to its size and the limited life expectancy of flexible tubing.

To date, no other centrifugal pump designs are known to provide the needed low flow rate and low head rise for such an application. Accordingly, the goal of the present invention is to address this severe shortage of donor kidneys by providing a small blood pump for a dialysis device which is portable and/or implantable.

DISCLOSURE OF INVENTION

The present invention provides a centrifugal pump having a very low specific speed and using a magnetic coupling for pumping the blood in a manner which reduces shear stresses and provides biocompatibility with the blood.

More specifically, the present invention provides a blood pump including a centrifugal impeller for pumping blood and a volute member enclosing the centrifugal impeller within a volute chamber. The centrifugal impeller and volute chamber are configured to provide a specific speed ($N_s$) of between approximately 500 and 600, wherein $$N_s = NQ^{0.5}/H^{0.75},$$

where

N=impeller rotative speed
Q=gallons per minute of flow
H=head rise, in feet

Preferably, the impeller includes a plurality of impeller blades having a ratio $R_b$ of approximately 6.75, wherein $R_b = I_l/I_w$, wherein $I_l$ is the radial length of the blades and $I_w$ is the axial width of the blades. Of course, this ratio $R_b$ could vary within the scope of the present invention. As the ratio $R_b$ increases, the specific speed decreases. With a ratio $R_b$ of 6.75, the specific speed $N_s$ is 550.

The blood pump includes biocompatible materials to enable implantation. All surfaces of the pump which contact blood are manufactured from titanium 6AL4V ELI alloy. The pump configuration is unique because it is the first centrifugal impeller style pump that was designed specifically for use in a dialysis device.

In addition, the same design philosophy has been used to design a blood pump with a flow capacity of four liters per minute. This higher flow rate blood pump has the potential to be used as a ventricular assist pump for cardiac patients awaiting heart transplant.

Accordingly, one object of the invention is to create a small blood pump for a portable dialysis unit.

A further object is to provide a pump having the required low flow rate and low head rise in a compact design which is biocompatible for use in an implantable dialysis device.

The above objects and other objects, features and advantages of the present invention are readily apparent from the following detailed description of the best mode for carrying out the invention when taken in connection with the accompanying drawings.

BRIEF DESCRIPTION OF DRAWINGS

FIG. 3 shows a plan view of an impeller corresponding with the pump of FIG. 1;

FIG. 4 shows an enlarged side view taken at line 4—4 of FIG. 3;

FIG. 5 shows a vertical cross-sectional view of the impeller of FIG. 3;

FIG. 6 shows a vertical cross-sectional view of a volute member used in the pump of FIG. 1;

FIG. 7 shows a cross-sectional view of a volute back face used in the pump of FIG. 1; and FIG. 8 shows a plan view of the volute back face of FIG. 7.

BEST MODE FOR CARRYING OUT THE INVENTION

Figure 1:
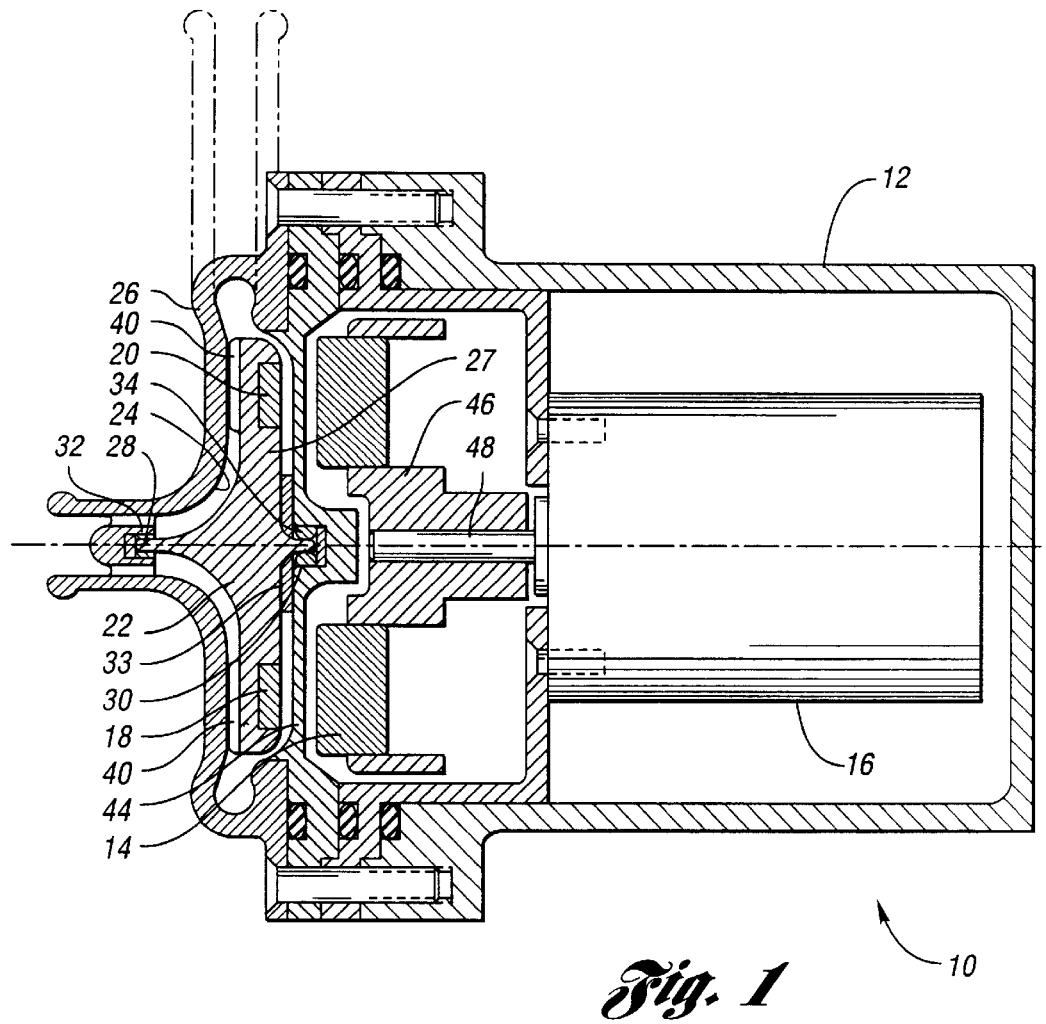
FIG. 1 shows a longitudinal cross-sectional view of a centrifugal blood pump in accordance with the present invention.

Referring to FIG. 1, a centrifugal pump 10 is shown in accordance with the present invention for pumping blood as part of a dialysis system, or a left ventricular assist pump. The pump includes a case 12 which houses a magnetic drive 14, driven by a 6 volt DC electric motor 16. The magnetic drive 14 magnetically engages magnets 18,20, which are imbedded in the impeller 22 for rotating the impeller 22. The impeller 22 is enclosed and rotates within a volute chamber 24 formed in a volute member 26. The impeller 22 includes front and rear stub shafts 28,30, which are supported, respectively, by front and rear bearings 32,34.

The centrifugal pump is sealless since there is no direct coupling between the drive motor 16 and the pump impeller 22. Instead, the pump features the magnetic coupling between the magnetic drive 14, which comprises four magnets on the drive motor shaft, and the tiny magnets 18,20 on the impeller 22 for driving the impeller. This eliminates the need for a dynamic shaft seal, and, therefore, eliminates the possibility of leakage of blood through the seal and eventually outside the pumping device. The magnets are of the permanent magnet variety made out of neodymium-iron-boron, a rare earth material. The four magnets 18,20 imbedded in the impeller 22 are 0.1875 inches in diameter by 0.065 inches thick. The magnets 18,20 are secured to the impeller 22 by an adhesive, such as a Master Bond Polymer System EP3HTMED, which is a medical adhesive, available from Master Bond, Inc. of Hackensack, N.J. The magnets that comprise the magnetic drive 14 are larger permanent magnet rare earth magnets which are 0.375 inches in diameter and 0.020 inches thick.

The bearings 32,34 are made of ruby which is precision machined and polished. The ruby bearings support the stub shafts 28,30, which are preferably 0.030 inch in diameter, and have a diamond-like coating, such as DLC, available from Diamonex, Inc. of Allentown, Pa. This diamond-like coating reduces wear on the stub shafts 28,30.

An axial thrust bearing 33 is also provided to offset any residual loads in the direction of the pump axis of rotation. The magnetic coupling produces a load in the axial direction which is partially offset by hydraulic loads produced by the pumped fluid. However, not all of the magnetic load is offset, so there remains a net (non-zero) residual load in the direction of the electric motor. The purpose of the axial thrust bearing 33 is to offset this residual load and to prevent early wear on the impeller shaft. The bearing 33 is made of highly polished sapphire, and is attached to the rear bearing housing 44, described below. The bearing 33 is made by Microlap Technologies, Inc. of Rolla, N. Dak.

As shown in FIG. 3, the pump impeller 22 is a one-piece titanium alloy construction and consists of the eight straight impeller blades 40, the disk 27, and the front and rear stub shafts 28,30. The impeller blades 40 have been optimized to provide minimum incidence with the flow and maximum pressure rise at the design operating condition. As illustrated in FIG. 4, the blades 40 are 0.04 inches high (h) and 0.040 inches wide (w), and have a radius (r) of 0.020 inches.

The pump rear cover and rear bearing housing 44, shown in FIGS. 1, 7 and 8, houses the rear bearing 34. This part features an O-ring seal that prevents the blood from leaking out. The forward facing side of this part has a highly polished surface finish of 8 RMS to prevent blood from adhering to it and depositing onto it.

The coupling 46, shown in FIG. 1, houses the four drive magnets which comprise the magnetic drive 14. The coupling 46 is connected to the motor shaft 48.

The case 12 hermetically seals the electric motor 16 and the magnetic drive 14. This part has been designed in anticipation of eventually implanting the kidney pump. The case 12 includes a biocompatible O-ring seal that will prevent body fluids from entering the motor and coupling.

Referring to FIG. 6, the volute chamber 24 of the volute member 26 is manufactured of a titanium 6AL4V ELI material, which is the same as the material used to manufacture the impeller, and is provided with a surface finish of 16 RMS.

Since blood is sensitive to shear stresses, large clearances are provided between the stationary and moving parts (i.e. the front case with volute chamber 24 and impeller 22), and the high surface finishes on the impeller and rear bearing reduce the likelihood of clotting and blood collection on these components.

The design point flow rate for the centrifugal blood pump 10 is 0.40 liters per minute (0.16 gallons per minute), which may be the lowest design point flow rate ever for a centrifugal pump. The design point "specific speed" ($N_s$) of the blood pump is 550 (or between approximately 500 and 600), and may also be the lowest that has ever been designed for a centrifugal pump. The specific speed $N_s$ is defined by the following equation:

$$N_s = \frac{NQ^{0.5}}{H^{0.75}}$$

where
N=impeller rotative speed (3,000)
Q=gallons per minute of flow (0.16)
H=head rise (2.8 feet).

Figure 2:
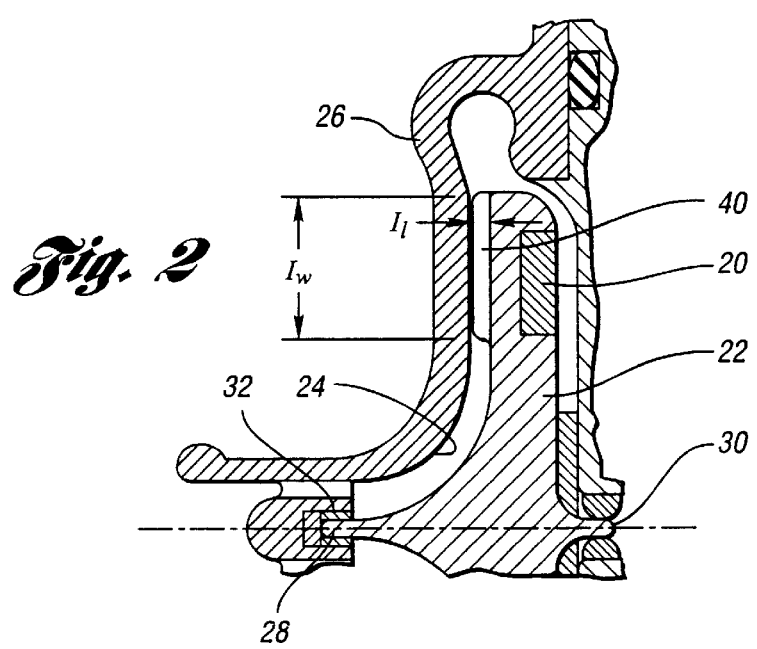
FIG. 2 shows a partial cross-sectional view taken from FIG. 1.

This very low specific speed can be attributed partially to the geometric shape of the centrifugal impeller blade. The shape of the impeller blade, in the meridional view shown in FIG. 2, can be defined by the ratio of two parameters: the axial width $I_w$ of the impeller and its length $I_l$ from inlet to exit. The axial width $I_w$ of each blood pump impeller blade 40 is approximately 0.040 inches and the length $I_l$ from inlet to exit is approximately 0.270 inches. The ratio of these two quantities ($R_b = I_l/I_w$) is equal to 6.75 and is considered high for a centrifugal impeller. It is this high ratio of geometric parameters that results in the very low impeller specific speed of approximately 550.

The design intent pressure or head rise of the pump is 70 millimeters of mercury. The pressure rise is required to overcome the losses and resistance to the flow through a dialysis "filter" device. The "filter" consists of a cluster of porous tubes that enable the exchange of fluids between the bloodstream and the cleansing fluid.

While the best mode for carrying out the invention has been described in detail, those familiar with the art to which this invention relates will recognize various alternative designs and embodiments for practicing the invention within the scope of the appended claims.

What is claimed is:

1. A blood pump comprising:
    a centrifugal impeller for pumping blood; and
    a volute member enclosing the centrifugal impeller within a volute chamber;
    wherein the centrifugal impeller provides a specific speed ratio ($N_s$) of between approximately 500 and 600 via a plurality of impeller blades having a ratio $R_b$ of approximately 6.75, wherein $R_b = I_l/I_w$ where $I_l$ is the radial length of the blades and $I_w$ is the axial width of the blades, wherein $$N_s = \frac{NQ^{0.5}}{H^{0.75}}$$

where
    N=impeller rotative speed in revolutions per minute (RPM)
    Q=gallons per minute (GPM) of flow, and
    H=head rise in feet of blood.

2. The blood pump of claim 1, further comprising at least one magnet secured to the centrifugal impeller, and a magnetic drive member operative to rotate the impeller.

3. The blood pump of claim 1, wherein said centrifugal impeller includes stub shafts at opposing sides thereof, each said shaft having a shaft diameter of less than approximately 0.10 inch.

4. The blood pump of claim 3, wherein said stub shafts have a shaft diameter of approximately 0.030 inch.

5. The blood pump of claim 4, wherein said stub shafts include a diamond-like coating and are supported by ruby bearings.

6. The blood pump of claim 5, wherein said diamond-like coating is approximately 3 to 5 microns thick.

7. The blood pump of claim 3, wherein said stub shafts are enclosed so that no dynamic shaft seal is needed, which eliminates the possibility of blood leaking from the pump.

8. The blood pump of claim 1, wherein said specific speed ratio $N_s$ is approximately 550.

9. The blood pump of claim 1, wherein said impeller and volute member comprise a biocompatible titanium material.

10. A blood pump for use in renal replacement therapy comprising:

a centrifugal impeller for pumping blood; and a volute member enclosing the centrifugal impeller within a volute chamber;

wherein the centrifugal impeller includes an arcuate profile for rotating within the volute chamber for minimizing incidence of the pumped blood and a plurality of impeller blades having a ratio $R_b$ of approximately 6.75 for further minimizing said incidence and to provide a desired specific speed, wherein $R_b = I_l/I_w$, where $I_l$ is the radial length of the blades and $I_w$ is the axial width of the blades.

11. The blood pump of claim 10, further comprising at least one magnet secured to the centrifugal impeller, and a magnetic drive member operative to rotate the impeller.

12. The blood pump of claim 10, wherein said centrifugal impeller includes stub shafts at opposing sides thereof, each said shaft having a shaft diameter of less than approximately 0.10 inch.

13. The blood pump of claim 12, wherein said stub shafts each have a shaft diameter of approximately 0.030 inch.

14. The blood pump of claim 13, wherein said stub shafts include a diamond-like coating and are supported by ruby bearings.

15. The blood pump of claim 14, wherein said diamond-like coating is approximately 3 to 5 microns thick.

16. The blood pump of claim 12, wherein said stub shafts are enclosed so that no dynamic shaft seal is needed, which eliminates the possibility of blood leaking from the pump.

17. The blood pump of claim 10, wherein said impeller and volute member comprise a biocompatible titanium material.

* * * * *